United States Patent
Poulsen et al.

(10) Patent No.: US 6,569,126 B1
(45) Date of Patent: May 27, 2003

(54) CYLINDER AMPOULE

(75) Inventors: Jens Ulrik Poulsen, Virum (DK); Jens Møller-Jensen, Copenhagen K (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/111,832

(22) Filed: Jul. 8, 1998

Related U.S. Application Data
(60) Provisional application No. 60/059,965, filed on Sep. 25, 1997.

(30) Foreign Application Priority Data

Jul. 14, 1997 (DK) ............................................. 0862/97

(51) Int. Cl.$^7$ ................................................ A61M 5/00
(52) U.S. Cl. ........................ 604/207; 604/224; 604/232; 604/228; 222/326; 222/390
(58) Field of Search ................................ 604/232, 211, 604/207, 209, 210, 181, 186, 197, 199, 218, 220–224, 228, 229, 263, 118, 235, 202, 244, 110, 38; 22/325–327, 386, 390, 137

(56) References Cited

U.S. PATENT DOCUMENTS

| | | | | |
|---|---|---|---|---|
| 3,215,320 A | | 11/1965 | Heisler ........................ 222/391 |
| 3,827,602 A | | 8/1974 | Nichoiis ...................... 222/137 |
| 4,381,779 A | * | 5/1983 | Margulies ................... 604/202 |
| 4,493,703 A | * | 1/1985 | Butterfield .................. 604/110 |
| 4,710,170 A | * | 12/1987 | Haber et al. ................ 604/110 |
| 4,973,318 A | * | 11/1990 | Holm et al. ................. 604/208 |
| 5,279,585 A | * | 1/1994 | Balkwill ..................... 222/309 |
| 5,300,041 A | * | 4/1994 | Haber et al. ................ 604/207 |
| 5,462,535 A | * | 10/1995 | Binnichsen et al. ........ 604/272 |
| 5,620,423 A | * | 4/1997 | Eykmann et al. ........... 604/217 |
| 6,221,046 B1 | * | 4/2001 | Burroughs et al. ......... 604/153 |

FOREIGN PATENT DOCUMENTS

| | | | |
|---|---|---|---|
| EP | 0 327 910 | * | 1/1989 |
| WO | WO 90/04424 | | 5/1990 |
| WO | WO 92/12747 | * | 8/1992 |

* cited by examiner

*Primary Examiner*—Brian L. Casler
*Assistant Examiner*—Cris L. Rodriguez
(74) *Attorney, Agent, or Firm*—Marc A. Began, Esq.; Richard W. Bork, Esq.; Reza Green, Esq.

(57) ABSTRACT

By a cylinder ampoule (1), comprising a tubular vessel with a membrane (4) sealingly closing one end and a piston (9) closing the other end, liquid stored between said piston (9) and said membrane (4) can be pressed out through an injection needle (7) piercing the membrane (4) when the piston (9) is pressed into the ampoule (1). The tube is made from a plastically deformable material. A pressure foot (10) on which a piston rod (13) is acting abuts the piston (9), carries a spring plate (11) made from a harder material than is the ampoule (1), is mainly perpendicular to the ampoule (1) axis, and has at least one diameter which is larger than the inner diameter of the ampoule (1) so that edges of the plate (11) abutting the inner wall of the ampoule (1) are deflected away from the piston (9) to form an acute angle with said wall. The ampoule (1) has an extension (14) beyond the position of the piston (9) by a full ampoule (1) and forms a part of a pen shaped syringe further comprising a dose setting and injection means co-operating with the piston rod (13).

4 Claims, 2 Drawing Sheets

CYLINDER AMPOULE

CROSS-REFERENCE TO RELATED APPLICATIONS

This application claims priority under 35 U.S.C. 119 of Danish application serial no. 0862/97 filed Jul. 14, 1997 and U.S. Provisional application serial No. 60/059,965 filed Sep. 25, 1997, the contents of which are fully incorporated herein by reference.

BACKGROUND OF THE INVENTION

The invention relates to cylinder ampoules of the type comprising a tubular vessel having a first end with a membrane sealingly closing this first end, and a second end closed by a piston which can be forced into the tube to press out a liquid, e.g. a medicine, stored in said tube between said piston and the membrane when an injection needle is mounted piercing the membrane.

This type of ampoule or cartridge is used in various types of syringes and manual or automatic medication apparatuses. The syringe may either be of a durable type, where the user changes the ampoule when it is empty, or they may be disposable in which case the ampoule is mounted in the syringe by the manufacturer and the whole device including the ampoule is disposed of when the ampule is empty. In automatic medication apparatuses the ampoule may be changed when it is empty or it may be a part of a disposable part comprising parts of the apparatus which have to be changed frequently, e.g., an infusion needle, a catheter, batteries etc. This way it is ensured that these parts are changed at least each time the ampoule is replaced.

In pen shaped syringes, it is desirable that the piston in the ampoule is blocked against backward movement when it has been pressed forward in the ampoule to press out a dose of medicine through a needle mounted at the neck end of the ampoule. Immediately after an injection has been made by pressing home an injection button, an internal pressure exists in the ampoule due to the elasticity of the piston and the flow resistance in the needle. This pressure subsides when the liquid has passed out through the needle and is absorbed in the tissue. However, if the pressure on the injection button is released before such an absorption is finished, the pressure in the ampoule will press the piston backward to relieve this pressure and the full set dose will not be injected.

Blocking of the piston against such backward movement is commonly obtained by providing a piston rod, through which the pressure is transmitted from the injection button to the piston, with teeth which are engaged by a pawl provided in the housing of the syringe. EP 327 910 describes a syringe for insulin injection by which the teeth on the piston rod each has a length corresponding to the distance the piston has to be advanced to obtain the injection of the minimal dose which can be set. I.e. the blocking of the piston against movement in a backward direction takes place in steps. A continuously acting blocking is obtained in the syringe described in WO 92/12747 wherein the blocking is performed by a sharp edged leaf spring which is mounted in the syringe housing and engages a smooth piston rod at an acute angle so that the piston rod may be passed forward to press the piston into the ampoule whereas an attempt to pass the piston rod backward will make the sharp edges of the leaf spring cut into the piston rod to stop further backward movement. If this analogue detent mechanism is used in syringes of the durable type the cutting marks which the leaf spring makes in the piston rod will soon make this piston rod appear rather as a toothed than a smooth rod.

It is an object of the invention to provide an ampoule of the kind described in the opening of this application and by which the detent blocking the piston against backward movement is attached to the disposable ampoule instead of relying on parts of the injection mechanism of the syringe.

This is obtained by an ampoule of the kind mentioned which is according to the invention characterised in that the ampoule tube is made from a plastically deformable material and that a pressure foot on which a piston rod is acting abuts an outer end of the piston and carries a spring plate which is mainly perpendicular to the ampoule axis and has at least one diameter which is larger than the inner diameter of the ampoule and where edges of the plate abutting the inner wall of the ampoule are deflected away from the piston to form an acute angle with said wall.

According to the invention the spring plate may be made of a harder material than is the ampoule, preferably from an elastic metal.

The parts of the spring plate abutting the inner wall of the ampoule may, due to the direction of their deflection, slide over the wall when the piston is pressed inwardly in the ampoule. If the piston attempts to move outwardly in the ampoule, the edges of the spring plate abutting the ampoule wall will cut into this wall and stop any outward movement of the piston. The cut marks left by the cutting edges of the spring plate in the wall of the ampoule will in all cases be disposed of when the ampoule is empty. Consequently, the cut marks will not be detrimental to the functioning of a new ampoule which replaces the used one. As the retraction detent is always positioned immediately behind the piston, a minimal tolerance is obtained insofar as the influence of the elasticity of the piston rod will not be added to the influence of the elasticity of the piston.

In an embodiment of the cylinder ampoule according to the invention the spring plate may be integral with the pressure foot. Further the piston rod may be integral with the pressure foot so that the piston, the spring plate, the pressure foot, and the piston rod forms an integral unit.

In another embodiment of the invention the spring plate is a rectangular leaf spring plate extending through a slot in the pressure foot and having diagonals which are longer that the inner diameter of the ampoule. The corners of the plate at the ends of the diagonals are deflected away from the piston towards the open end of the ampoule to form an acute angle with the ampoule wall when the pressure foot is pressed into the end of the ampoule to abut the piston. This construction allow the pressure foot to be moved inward in the ampoule by which movement the deflected corners will slide over the wall whereas an attempt to move the pressure foot outward will make the corners of the leaf spring plate bite into the wall of the ampoule to block any outward movement of the pressure foot.

Another object of the invention is to provide a rotation detent which prevents rotation relative to the ampoule. Such a rotation detent may be obtained by splitting up the spring plate so that the engagement between this plate and the ampoule wall takes place in a number of circumferentially spaced points or zones of the ampoule wall. When the plate cuts into the ampoule wall in such spaced zones the engaging parts of the plate have to force their ways through the parts of the ampoule wall separating the points or zones of engagement if the plate shall be rotated. This will yield a considerable resistance against rotational movement of the plate relative to the ampoule and elements coupled to the plate in a way preventing relative rotation of these elements and the plate will also be prevented from rotation relative to the ampoule.

Further according to the invention the ampoule may have an extension extending beyond the piston when the ampoule is full. This extension may surround the piston rod over the entire length of this rod.

The piston rod may be provided with an outer thread and the full ampoule may be extended behind the piston to surround the piston rod over its entire length. Provided with the features, the ampoule may form a main part of a pen shaped syringe, the syringe further comprising a dose setting and injection means cooperating with the piston rod and a cap covering at least a part of the ampoule and its extension. Such a syringe can be disposed of when the ampoule is empty.

According to an embodiment of the invention, the extension of the ampoule may on its inner wall be provided with a protrusion which cooperates with the dose setting and injection means to provide an audible and tactile indication of the setting of a dose and a stop defining the maximum dose which can be set.

Further, according to an embodiment of the invention, the extension at the transition from the ampoule to said extension is, along its perimeter, provided with equidistant axial recesses engaged by an axial spline at the inner wall of the cap, to block against relative rotation of the ampoule and the cap during the operation of the dose setting member. By this construction, the ampoule is rotationally fixed in the cap, and rotating the dose setting means relative to the cap causes the dose setting means to rotate relative to the ampoule and the piston rod.

According to still another embodiment of the cylinder ampoule according to the invention, an end edge of the extension is provided with a toothing comprising teeth having an abrupt leading edge and a ramp shaped trailing edge, which toothing cooperates with a corresponding toothing on an edge of a dose setting and injection button. By said toothings, it is ensured that the dose setting and injection button from its zero point can only be rotated in a direction by which a positive dose is set.

According to another embodiment of the invention, the cap fits over the ampoule and its extension and may abut the dose setting and injection button. The cap may have a recess in its abutting edge and a scale along this edge. The injection button has on its abutting edge a projection fitting into the recess in the injection button. When the cap is mounted with the protrusion on the dose setting and injection button engaging the recess of the cap, it is ensured that a marker on said protrusion points at the zero on a scale on the outer perimeter of the cap.

BRIEF DESCRIPTION OF THE DRAWINGS

In the following the invention will be described in further details with references to the drawing, wherein.

DETAILED DESCRIPTION OF THE INVENTION

Figure 1:
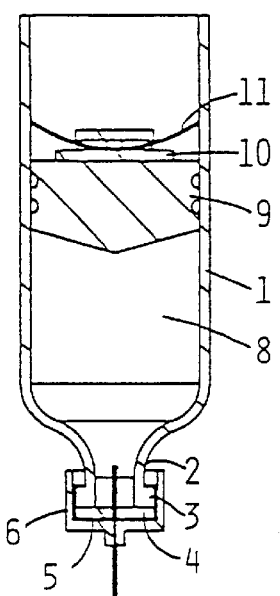
FIG. 1 shows a sectional view of a cylinder ampoule according to the invention with a detent mechanism allowing only unidirectional movement of the piston.

In FIG. 1 a cylinder ampoule 1 has end provided with a neck 2 which is at its outer end provided with a flange 3 against which a rubber membrane 4 is sealingly held by a metal cap 5 having an edge gripping behind the flange 3. The metal cap 5 forms a needle hub receiving part onto which a hub 6 carrying a double ended needle 7 is mounted with an end piercing the rubber membrane 4 and communicating with the inner space 8 of the ampoule 1.

Figure 2:
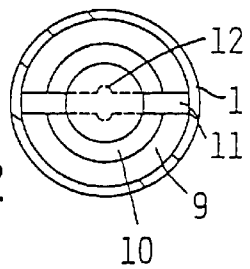
FIG. 2 shows a top view of the ampoule in FIG. 1.
Figure 4:
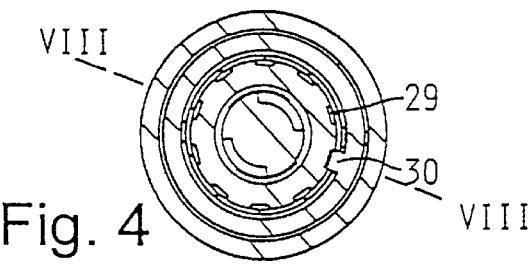
FIG. 4 shows a cross section along the line IV—IV in FIG. 3.
Figure 5:
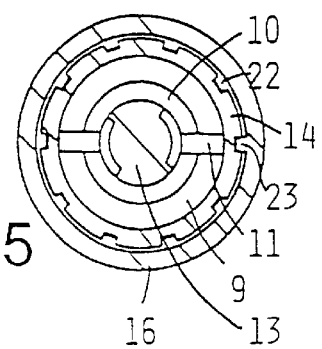
FIG. 5 shows a cross section view along the line V—V in FIG. 3.

The other end of the cylinder ampoule 1 is closed by a rubber piston 9 which is at its side turning away from the inner space 8 of the ampoule 1 backed up by a foot 10. The foot 10 is provided with a detent metal leaf spring plate 11 which is secured to the piston 9 in a slot. The metal leaf spring plate 11 is as it is seen in FIG. 2 provided with protrusions 12 engaging corresponding recesses in the foot 10 to ensure that the leaf spring plate 11 is not drawn out of the slot.

Such ampoules are mainly made from glass but the invention is based on the fact that the ampoule is made from a somewhat softer plastically deformable material into which the edges of a leaf spring may cut, e.g. a suitable plastic. The leaf spring is made from an elastic material which can cut into the plastic of the ampoule, e.g. metal or a hard plastic.

The piston 9 is backed up by a pressure foot 10 through which a pressure is transmitted to the piston 9 by, a piston rod in the device wherein the ampoule is used. In the shown embodiment the leaf spring plate 11 is formed as a rectangular elastic plate having diagonals which are slightly larger than the inner diameter of the ampoule so that the corners of the plate is deflected backward, i. e. away from the piston 9, when the foot 10 with the leaf spring plate 11 is pressed into the ampoule. Thereby the deflected corners form an acute angle with the inner wall of the ampoule 1 so that said corners may slide over said wall when the foot 10 with the leaf spring plate 11 is pressed inwards in the ampoule but will cut into said wall if an attempt is made to move the foot 10 with the leaf spring plate 11 outward towards the open end of the ampoule 1.

Figure 3:
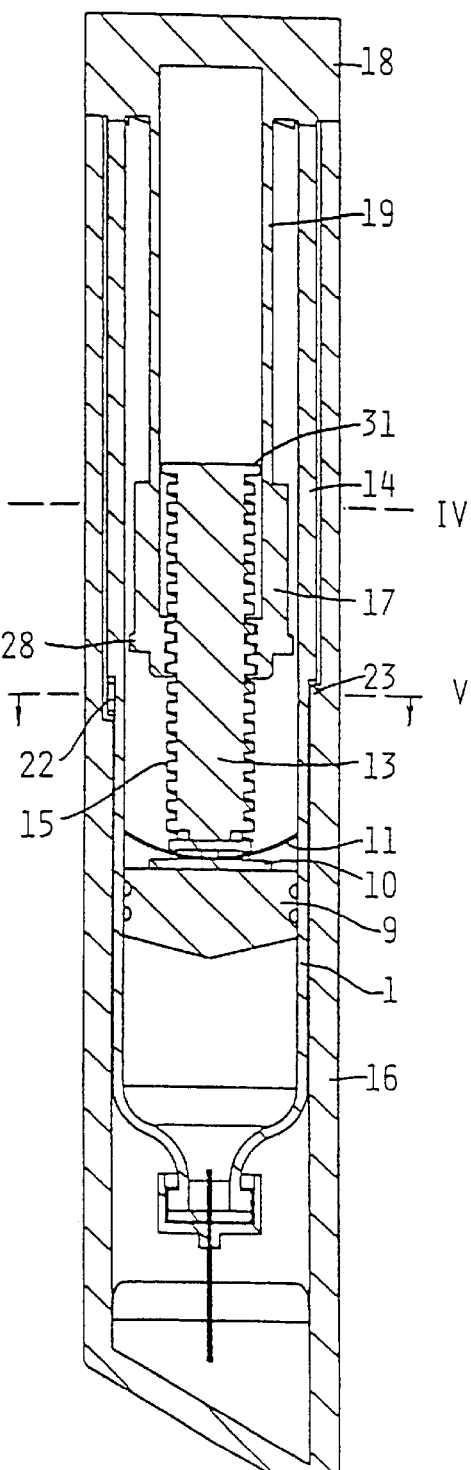
FIG. 3 shows a sectional view of a disposable syringe based on an embodiment of the cylinder ampoule according to the invention.

FIG. 3 shows a disposable pen shaped syringe which is based on a special embodiment of an ampoule according to the invention in which embodiment a threaded piston rod 13 is integral with the foot 10 and the ampoule 1 has an extension 14 extending beyond the outermost position of the piston 9 to form a tube surrounding the piston rod 13. The syringe works according to the principles known from the syringe described in EP 327 910 where a dose is set by screwing a nut along a threaded piston rod to lift a button connected to the nut away from a stop, and where the set dose is injected by pressing the button home to abutment with the stop. In the following the syringe according to FIG. 3 will be further described the elements already known from FIG. 1 being allocated the same reference numbers as in FIG. 1.

Figure 6:
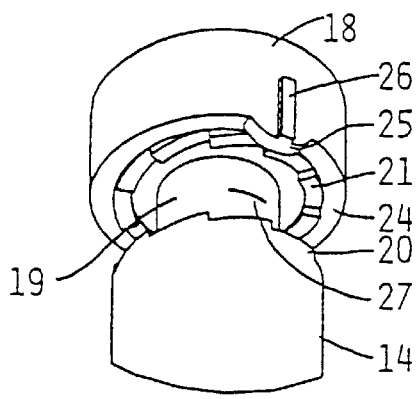
FIG. 6 shows a perspective view of a detail of the syringe in FIG. 3.

An ampoule 1 has at its open end an extension 14. The piston 9 closing the open end of the ampoule 1 is provided with a foot 10 carrying a piston rod 13 which has an outer thread 15. A leaf spring plate 11 is mounted in a slot through the foot 10 to allow only inward movement of said foot and the piston 9 in the ampoule 1 as the corners of the spring plate 11 cut into the walls of the ampoule 1 which is made from e.g. plastic. As the corners of the leaf spring plate 11 cuts into the ampoule walls also rotation about the longitudinal axis of the ampoule is blocked so that a piston rod guide like those which are commonly used to make a piston rod inrotatable relative to the housing can be omitted. The ampoule 1 with its extension 14 forms the housing of the syringe and only a dose setting and injection member and a protecting cap 16 has to be added. The cap is 16 is tubular and fits over the ampoule 1 and its extension 14. The dose setting and injection means comprise a nut member 17, a button 18, and a tubular member 19 connecting the button 18 and the nut member 17. The nut member 17 has an internal thread and is mounted with this internal thread engaging the outer thread 15 of the piston rod 13. The tubular member 19 runs inside the extension 14 coaxial with this extension and connects the nut member 17 to the button 18 which lies outside the extension 14 but in abutment with the end of this extension 14. The abutting edges of the extension 14 and the button 18 are provided with engaging toothings which have teeth, 20 and 21 respectively, with ramp shaped leading edges and an abrupt trailing edges as shown in FIG. 6. These toothings ensure that the button can from its abutment position only be rotated in the direction by which the button is lifted away from the extension and not in the direction by which the piston is drawn outward in the ampoule.

Figure 7:
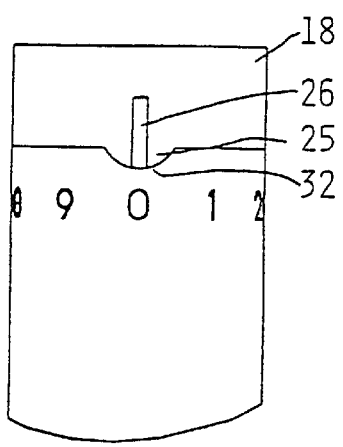
FIG. 7 shows a detail of the syringe in FIG. 3.
Figure 8:
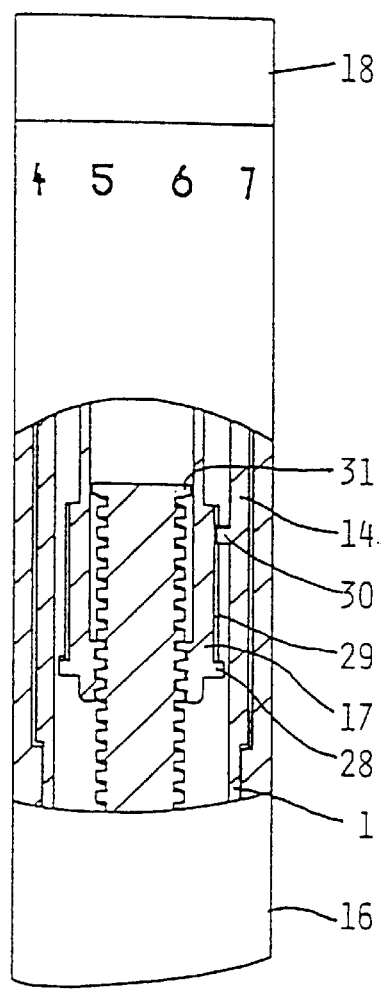
FIG. 8 shows a partly sectional view of the syringe in FIG. 3 seen in the direction indicated by line VIII—VIII in FIG. 4.
Figure 9:
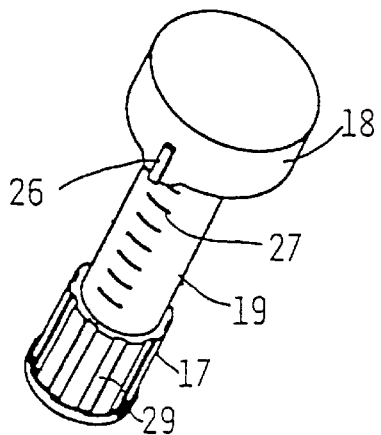
FIG. 9 shows a part comprising a nut member and a press button and a connecting tubular element.

The button 18 has an outer diameter corresponding to the outer diameter of the cap 16 and the outer cylindrical wall of the button 18 is flush with the outer cylindrical wall of the cap 16 when this cap is mounted on the ampoule 1 with its edge abutting against an outer edge 24 of the button. As shown in FIG. 7, a projection 25 on this outer edge 24 must engage a recess 32 in the edge of the cap 16 to obtain said abutment. This way it is ensured that the cap 16 is always mounted with its recess 32 opposite the projection 25. The projection is provided with a pointer 26 pointing at a scale along the edge of the cap 16. This scale has its zero at said recess so that the pointer 26 will point at zero on the scale when the cap is mounted.

The extended ampoule is at the transition between the very ampoule 1 and the extension 14 provided with a number of longitudinal recesses 22 distributed equidistantly along the perimeter of the ampoule. A protrusion 23 on the inner wall of the tubular cap 16 engages one of the recesses 22 to block rotation of the cap relative to the ampoule.

When a dose is going to be set, the cap 16 is displaced axially to bring the projection 25 out of engagement with the recess 32 in the edge of the cap 16. The projection and the recess may have sloping edges so that the projection 25 automatically slides out of the recess 32 and push the button 18 and the cap 16 away from each other when it is attempted to rotate the button and the cap relative to each other. It shall be noticed that such rotation may only be made in one direction due to the engaging toothings on the cap and the button. The dose is set by this rotation of the button relative to the cap and the size of the dose may be read on the scale along the edge of the cap 16. Due to the fact that the cap due to the engagement of the recesses 22 and the protrusion 23 is inrotatable relative to the ampoule and that the piston rod due to the spring plate 11 biting into the ampoule wall is inrotatable relative to the ampoule, the nut member is rotated relative to the piston rod 13 when the cap 16 and the button 18 is rotated relative to each other. The allowed direction of rotation is chosen so that the nut will move up along the piston rod and lift the button 18 up from the edge of the extension 14 of the ampoule 1 as shown in FIG. 6.

As one revolution of the button will make the pointer 26 point at zero again, marks 27 on the tubular member 19 may indicate the numbers of revolution of the button 18 so that the doses corresponding to the full revolutions can be added to the dose shown on the scale.

The outer side of the nut member 17 is along it's perimeter provided with a number of equidistant recesses 29 corresponding to the number of positions on the scale, and a tooth shaped protrusion 30 on the inner wall of the extension 14 of the ampoule 1 enables a releasable locking of the nut member 17 relative to the ampoule at each position of the pointer 26 relative to the scale. The locking is obtained by the protrusion 30 engaging one of the recesses 29 and the unlocking is obtained when said protrusion during further rotation is pressed out of the recess against the resilience of the extension to engage the next recess. By this locking mechanism an audible and tactile indication of the dose setting is obtained.

Figure 10:
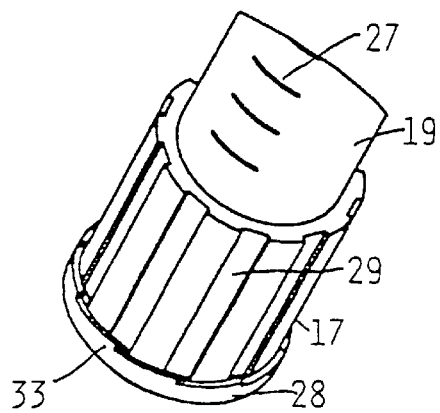
FIG. 10 shows in enlarged scale a detail comprising the nut member in FIG. 9.

When the nut member is screwed up along the piston rod, this movement is stopped when an annual outer flange 28 on the nut member 17 abuts the tooth shaped protrusion 30 on the inner wall of the extension of the ampoule. The abutting surface of the protrusion 30 is shaped with an abrupt leading edge and a ramp shaped trailing edge to form a tooth which engages corresponding teeth 33, shown in FIG. 10, on the abutting surface of the flange 28. By this precaution the stopping is obtained by mutual abutment of abrupt leading edges of a pair of teeth and is this way made well defined. Another stop is provided by an end plate 31 at the end of the piston rod 13. The thread of the nut member cannot pass this end plate and this way it is ensured that a set dose does not exceed the volume remaining in the ampoule.

What is claimed is:

1. A cylinder ampoule comprising: a tubular vessel having a first end, a second end, and an inner wall; a membrane for sealing and closing the first end of the vessel; a piston having a first and second end, the piston closing the second end of the vessel so that a liquid can be stored in the vessel between the first end of the piston and the membrane and can be pressed out through an injection needle inserted through the membrane when the piston is forced into the tubular vessel; wherein the tubular vessel is made from a plastically deformable material; and further comprises a spring plate made of a material harder than the material of the vessel and a pressure foot, wherein the spring plate is carried by the pressure foot and is mainly perpendicular to the longitudinal axis of the vessel; and wherein the spring plate has at least one diameter that is larger than the diameter of the vessel inner wall so that edges of the plate abut tile inner wall of the vessel and are deflected away from the piston to form an acute angle with the inner wall; and wherein the spring plate is split up to engage the vessel inner, wall in a number of circumferentially spaces, points, or zones.

2. An apparatus comprising: a cylinder ampoule comprising: a tubular vessel having a first end, a second end, and an inner wall; a membrane for sealing and closing the first end of the vessel; a piston having a first and second end, the piston closing the second end of the vessel so that a liquid can be stored in the vessel between the first end of the piston and the membrane and can be pressed out through an injection needle inserted through the membrane when the piston is forced into the tubular vessel; wherein the tubular vessel is made from a plastically deformable material; and further comprises a spring plate made of a material harder than the material of the vessel and a pressure foot, wherein the spring plate is carried by the pressure foot and is mainly perpendicular to the longitudinal axis of the vessel; and wherein he spring plate has at least one diameter that is larger than the diameter of the vessel inner wall so that edges of the plate abut the inner wall of the vessel and are deflected away from the piston to form an acute angle with the inner wall; and wherein the apparatus further comprises a piston rod that is integral with the pressure foot and extends in the longitudinal direction of the vessel away from the second side of the piston; and wherein the apparatus further comprises a dose setting for setting a dose and injection mechanism for driving the piston rod to administer the set dose, wherein the dose setting and injection mechanism comprises a nut member having an inner thread; and wherein the piston rod is provided with an outer thread engaging the inner thread of the nut member and wherein the ampoule has an inner wall having a protrusion, and wherein the nut member has a plurality of longitudinal recesses for selectively receiving the protrusion to provide an audible and tactile indication of the setting of a dose and wherein the protrusion further cooperates with the nut member to act as a stop defining the maximum dose that can be set.

3. The apparatus of claim 2, wherein the ampoule has an edge provided with a toothing comprising teeth having an abrupt leading edge and a ramp shaped trailing edge and wherein said dose setting mechanism includes a does setting and injection button having an edge containing toothing that cooperates with the toothing on the ampoule edge to allow rotation of the dose setting and injection button relative to the ampoule in only one direction when the toothings engage one another.

4. The apparatus of claim 3, further comprising a removable cap that fits over the ampoule and has a cap edge that abuts the dose setting and injection button, wherein the cap has a recess and a scale along the cap edge and wherein the dose setting and injection button includes a projection fitting in the recess when the cap is mounted on the ampoule.

* * * * *

UNITED STATES PATENT AND TRADEMARK OFFICE
CERTIFICATE OF CORRECTION

PATENT NO. : 6,569,126 B1
APPLICATION NO. : 09/111832
DATED : May 27, 2003
INVENTOR(S) : Poulsen et al.

Page 1 of 1

It is certified that error appears in the above-identified patent and that said Letters Patent is hereby corrected as shown below:

Claim 1

Column 6, Line 52

Change "tile" to --the--

Column 6, Line 55

Delete "," after "inner"

Claim 2

Column 7, Line 4

Change "wherein he" to --wherein the--

Signed and Sealed this

Twenty-third Day of October, 2007

JON W. DUDAS
*Director of the United States Patent and Trademark Office*